(12) United States Patent
Peters et al.

(10) Patent No.: US 7,045,522 B2
(45) Date of Patent: May 16, 2006

(54) 8-AZABICYCLO[3.2.1]OCT-2-ENE AND -OCTANE DERIVATIVES TECHNICAL FIELD

(75) Inventors: Dan Peters, Malmo (SE); Gunnar M. Olsen, Frederiksberg (DK); Simon Feldbaek Nielsen, Herlev (DK); Elsebet Ostergaard Nielsen, Kobenhaven K (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 10/726,680

(22) Filed: Dec. 4, 2003

(65) Prior Publication Data

US 2004/0116703 A1 Jun. 17, 2004

Related U.S. Application Data

(60) Division of application No. 09/864,367, filed on May 25, 2001, now Pat. No. 6,680,328, which is a continuation of application No. PCT/DK99/00661, filed on Nov. 26, 1999.

(30) Foreign Application Priority Data

Nov. 27, 1998 (DK) ............................... 1998 01570

(51) Int. Cl.
*A61K 31/46* (2006.01)
*A61K 31/4709* (2006.01)
*C07D 451/02* (2006.01)

(52) U.S. Cl. ................ 514/248; 514/249; 514/304; 514/299; 544/235; 544/237; 544/353; 546/112; 546/126

(58) Field of Classification Search ................ 546/126, 546/112; 544/235, 237, 353; 514/304, 299, 514/249, 248
See application file for complete search history.

(56) References Cited

U.S. PATENT DOCUMENTS 5,919,932 A * 7/1999 Gaster et al. ............... 546/112

6,107,307 A 8/2000 Audia ........................ 514/304

FOREIGN PATENT DOCUMENTS

| WO | A1-9713770 | 4/1997 |
|----|------------|--------|
| WO | A1-9854181 | 3/1998 |
| WO | WO 98/46600 A1 | 10/1998 |
| WO | WO 99/65492 A1 | 12/1999 |
| WO | WO 00/04017 A | 1/2000 |
| WO | WO 2000/045846 A | 8/2000 |
| WO | 0192259 | 12/2001 |

OTHER PUBLICATIONS

Holladay et al. J. Med. Chem. 1997, 40:4169-4188.*
Levin ED. Psychopharmacology 1998, 138(3-4): 217-30 (abstract).*
Grant et al., Grant and Hackh's Chemical Dictionary, Mc Graw- Hill Book Company, p. 78 (1987).*
David B Repke et al., Journal of Organic Chemistry, vol. 59, (1994), pp. 2164-2171. XP002288833.
R.G. Glushkov et al., Chemical Abstracts, vol. 84, No. 25, (Jun. 21, 1976), abstract No. 180439r, XP002288836 and Khim.-Farm. Zh., vol. 9, No. 12 (1975), XP002288837.
Kurt Freter, Journal of Organic Chemistry, vol. 40, No. 17, (1975), pp. 2525-2529, XP002288834.
Rudolf Tschesche et al., Chemische Berichte, vol. 90, (1957), pp. 579-585.

* cited by examiner

*Primary Examiner*—Bernard Dentz
(74) *Attorney, Agent, or Firm*—Birch, Stewart, Kolasch & Birch, LLP

(57) ABSTRACT

The present invention relates to novel 8-azabicyclo[3.2.1] oct-2-ene and -octane derivatives which are found to be cholinergic ligands at the nicotinic Acetyl Choline Receptors.

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

3 Claims, No Drawings

8-AZABICYCLO[3.2.1]OCT-2-ENE AND -OCTANE DERIVATIVES TECHNICAL FIELD

TECHNICAL FIELD

The present application is a divisional of U.S. patent application Ser. No. 09/864,367, filed May 25, 2001, now U.S. Pat. No. 6,680,328 which is a continuation of International Application No. PCT/DK99/00661, filed Nov. 26, 1999, the entire contents of which are hereby incorporated by reference.

The present invention relates to novel 8-azabicyclo[3.2.1]oct-2-ene and -octane derivatives which are found to be cholinergic ligands at the nicotinic Acetyl Choline Receptors.

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic ACh receptors dominate quantitatively over nicotinic ACh receptors in the brain area important to memory and cognition, and much research aimed at the development of agents for the treatment of memory related disorders have focused on the synthesis of muscarinic ACh receptor modulators.

Recently, however, an interest in the development of nicotinic ACh receptor modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

The present invention is devoted to the provision novel nicotinic receptor modulators useful for therapy or diagnosis, which modulators are structurally close analogues of the compounds described in WO 98/54181 (NeuroSearch A/S).

SUMMARY OF THE INVENTION

The present invention is devoted to the provision novel nicotinic receptor modulators, which modulators are useful for the treatment of diseases or disorders related to the cholinergic receptors, and in particular the nicotinic ACh receptor (nAChR).

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides chemical compounds having the general formula

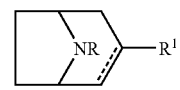

(I)

in labelled or unlabelled form, or any of its enantiomers or any mixture thereof, or a pharmaceutically acceptable salt thereof;

wherein

- - - - represents a single or a double bond;

R represents hydrogen, alkyl, alkenyl, alkynyl, cycloalkyl, cycloalkylalkyl, a mono- or polycyclic aryl group, or aralkyl; and $R^1$ represents a group of the formula

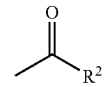

wherein $R^2$ represents hydrogen, alkyl, alkenyl, alkynyl, cycloalkyl, cycloalkyl-alkyl, amino or a fluorescent group; or $R^1$ represents an mono- or polycyclic aryl group, which aryl group is substituted one or more times with substituents selected from the group consisting of alkyl, cycloalkyl, cycloalkyl-alkyl, alkenyl, alkynyl, methylenedioxy, hydroxy, alkoxy, alkoxy-alkyl, alkoxy-alkoxy, aryloxy, alkylcarbonyloxy, halogen, $OCF_3$, CN, amino, carbamoyl, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group; or $R^1$ represents a monocyclic 5- or 6-membered, saturated, partially saturated or unsaturated heterocyclic group, which heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, alkylcarbonyloxy, halogen, $CF_3$, $OCF_3$, CN, sulfanyl, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group; or $R^1$ represents a bi-cyclic heterocyclic group composed of a monocyclic 5- or 6-membered heterocyclic group with one heteroatom, fused to a benzene ring or fused to another monocyclic 5- or 6-membered, saturated, partially saturated or unsaturated heterocyclic group, all of which is substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, alkylcarbonyloxy, halogen, $CF_3$, $OCF_3$, CN, sulfanyl, amino, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group.

In a second aspect the invention provides pharmaceutical compositions comprising a therapeutically effective amount of the chemical compound of the invention or a pharmaceutically acceptable addition salt thereof, together with at least one pharmaceutically acceptable carrier or diluent.

In a third aspect the invention provides an assay kit comprising the composition according to the invention in a unit dosage form in a suitable container.

In a fourth aspect the invention relates to a use of the chemical compound of the invention for the manufacture of a medicament for the treatment or alleviation of a disease or disorder of a living animal body, including a human, which disease or disorder is responsive to the action of a nicotinic Acetyl Choline Receptor (nAChR) modulator.

A fifth aspect of the invention relates to the use of the chemical compound of the invention or any of its enantiomers or any mixture thereof, in labelled or unlabelled form, for the manufacture of a diagnostic agent for the diagnosis of a disorder or disease of a living animal body, including a human, which disease or disorder is responsive to the action of a nicotinic Acetyl Choline Receptor (nAChR) modulator, or a serotonin receptor modulator.

A sixth aspect of the invention provides a method for the preparation of the compounds according to the invention, which method comprises A) the step of reacting a compound having the formula

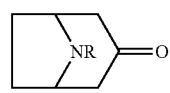

(II)

wherein R is as defined herein,
with a compound of the formula $R^1$—Li,
wherein $R^1$ is as defined herein,
followed by dehydration of the compound obtained; or B) the step of reacting a compound having the formula

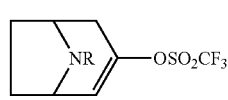

(III)

wherein R is as defined herein,
with a compound of formula $R^1$—X,
wherein $R^1$ is as defined herein,
and X represents halogen, boronic acid, or trialkylstannyl; or C) the step of reducing a compound having the formula

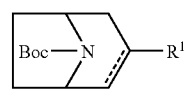

(IV)

wherein $R^1$ is as defined herein.

A seventh aspect of the invention provides a method of the treatment or alleviation of a disease or disorder of a living animal body, including a human, which disease or disorder is responsive to the action of a nicotinic Acetyl Choline Receptor (nAChR) modulator, which method comprises the step of administering to such a living animal body, including a human, in need thereof a therapeutically effective amount of the chemical compound of the invention A last aspect of the invention provides a method for the non-invasive determination of the distribution of a tracer compound inside a whole, intact living animal or human body using a physical detection method, wherein the tracer compound is a compound according to the invention or any of its enantiomers or any mixture thereof, or a pharmaceutically acceptable salt thereof, in labelled or unlabelled form.

Other objects of the invention will be apparent to the person skilled in the art from the following detailed description and examples.

DETAILED DISCLOSURE OF THE INVENTION

Novel 8-azabicyclo[3.2.1]oct-2-ene and -octane Derivatives

In its first aspect the invention provides novel 8-azabicyclo[3.2.1]oct-2-ene or -octane derivatives. The 8-azabicyclo [3.2.1]oct-2-ene and -octane derivatives of the invention may be characterised by being a chemical compound of the general formula 1:

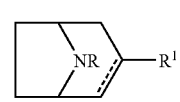

(I)

in labelled or unlabelled form, or any of its enantiomers or any mixture thereof, or a pharmaceutically acceptable salt thereof;
wherein
----- represents a single or a double bond;
R represents hydrogen, alkyl, alkenyl, alkynyl, cycloalkyl, cycloalkylalkyl, a mono- or polycyclic aryl group, or aralkyl; and
$R^1$ represents a group of the formula

wherein $R^2$ represents hydrogen, alkyl, alkenyl, alkynyl, cycloalkyl, cycloalkyl-alkyl, amino, or a fluorescent group; or $R^1$ represents an mono- or polycyclic aryl group, which aryl group is substituted one or more times with substituents selected from the group consisting of alkyl, cycloalkyl, cycloalkyl-alkyl, alkenyl, alkynyl, methylenedioxy, hydroxy, alkoxy, alkoxy-alkyl, alkoxy-alkoxy, aryloxy, alkylcarbonyloxy, halogen, $OCF_3$, CN, amino, carbamoyl, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group; or $R^1$ represents a monocyclic 5- or 6-membered, saturated, partially saturated or unsaturated heterocyclic group, which heterocyclic group may be substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, alkylcarbonyloxy, halogen, $CF_3$, $OCF_3$, CN, sulfanyl, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group; or $R^1$ represents a bi-cyclic heterocyclic group composed of a monocyclic 5- or 6-membered heterocyclic group with one heteroatom, fused to a benzene ring or fused to another monocyclic 5- or 6-membered, saturated, partially saturated or unsaturated heterocyclic group, all of which is substituted one or more times with substituents selected from the group consisting of alkyl, cycloalkyl, cycloalkylalkyl, alkenyl, alkynyl, methylenedioxy, hydroxy, alkoxy, alkoxy-alkyl, alkoxy-alkoxy, aryloxy, alkylcarbonyloxy, halogen, $CF_3$, $OCF_3$, CN, sulfanyl, amino, nitro, a mono- or polycyclic aryl group, a monocyclic 5- or 6-membered, saturated, partially saturated or unsaturated heterocyclic group, and a group of the formula —X—R'(—Y—R")$_n$; wherein X and Y independently of each another represent oxygen or sulphur, n is 0, 1 or 2, and R' and R" independently of each another represent alkyl or cycloalkyl; or a fluorescent group.

In a preferred embodiment the compound of the invention is represented by the general formula (I) wherein $R^1$ represents a 1-naphthyl group, a 2-naphthyl group, a 3-naphthyl group or a 4-naphthyl group; which naphthyl groups may be substituted one or more times at the 5, 6, 7 or 8-positions.

In a more preferred embodiment the compound of the invention is represented by the general formula (I) wherein R represents hydrogen or alkyl; and $R^1$ represents a 1-naphthyl group or a 2-naphthyl group; which naphthyl groups may be substituted one or more times with substituents selected from the group consisting of halogen, amino, hydroxy, alkoxy, alkoxy-alkoxy, alkoxy-alkyl, alkylcarbonyloxy, sulfanyl, alkylsulfanyl, alkylsulfanyl-alkoxy, alkoxy-alkylsulfanyl, alkylsulfanyl-alkylsulfanyl, pyrrolidinyl, piperidinyl, piperazinyl, and homopiperazinyl.

In a yet more preferred embodiment the compound of the invention is represented by the general formula (I) wherein $R^1$ represents acetoxy-naphthyl, methoxy-naphthyl, hydroxy-naphthyl, bromo-naphthyl, methoxymethoxy-naphthyl, methoxyethoxy-naphthyl, ethylsulfanyl-naphthyl, methylsulfanyl-naphthyl, ethoxy-naphthyl, sulfanyl-naphthyl, methoxyethylsulfanyl-naphthyl, ethoxyethoxy-naphthyl, amino-naphthyl, dimethylamino-naphthyl, diethylamino-naphthyl, pyrrolidinyl-naphthyl, piperidinyl-naphthyl, piperazinyl-naphthyl, or homopiperazinyl-naphthyl.

In a most preferred embodiment the compound of the invention is (±)-3-[1-(2-Iodophenyl)]-8-methyl-8-azabicyclo[3.2.1]oct-2-ene;

(±)-3-[1-(2-Bromophenyl)]-8-methyl-8-azabicyclo[3.2.1]oct-2-ene;

(±)-3-[1-(2-Chlorophenyl)]-8-methyl-8-azabicyclo[3.2.1]oct-2-ene;

(±)-3-[1-(2-iodophenyl)]-8-methyl-8-azabicyclo[3.2.1]oct-2-ene;

(±)-3-[1-(2-bromophenyl)]-8-methyl-8-azabicyclo[3.2.1]oct-2-ene;

(±)-3-[1-(2-chlorophenyl)]-8-methyl-8-azabicyclo[3.2.1]oct-2-ene;

(±)-3-[6-(methoxy)-2-naphthyl]-8-methyl-8-azabicyclo[3.2.1]oct-2-ene;

(±)-3-[6-(hydroxy)-2-naphthyl]-8-methyl-8-azabicyclo[3.2.1]oct-2-ene;

(±)-3-[6-(2-methoxyethoxy)-2-naphthyl]-8-methyl-8-azabicyclo[3.2.1]oct-2-ene;

Exo-3-[6-(methoxymethoxy)-2-naphthyl]-8-methyl-8-azabicyclo[3.2.1]octane;

(±)-3-[6-(acetyloxy)-2-naphthyl]-8-methyl-8-azabicyclo[3.2.1]oct-2-ene;

(±)-8-methyl-3-[6-(ethylsulfanyl)-2-naphthyl]-8-azabicyclo[3.2.1]oct-2-ene;

(±)-8-methyl-3-[6-(methylsulfanyl)-2-naphthyl]-8-azabicyclo[3.2.1]oct-2-ene;

(±)-3-[6-(ethoxy)-2-naphthyl]-8-methyl-8-azabicyclo[3.2.1]oct-2-ene;

(±)-3-[6-(sulfanyl)-2-naphthyl]-8-methyl-8-azabicyclo[3.2.1]oct-2-ene;

(±)-3-[6-(2-methoxyethylsulfanyl)-2-naphthyl]-8-methyl-8-azabicyclo[3.2.1]oct-2-ene;

(±)-3-[6-(2-ethoxyethoxy)-2-naphthyl]-8-methyl-8-azabicyclo[3.2.1]oct-2-ene;

(±)-3-[6-bromo-2-naphthyl]-8-methyl-8-azabicyclo[3.2.1]oct-2-ene;

(±)-3-[6-amino-2-naphthyl]-8-methyl-8-azabicyclo[3.2.1]oct-2-ene;

(±)-3-[6-dimethylamino-2-naphthyl]-8-methyl-8-azabicyclo[3.2.1]oct-2-ene;

(±)-3-[6-diethylamino-2-naphthyl]-8-methyl-8-azabicyclo[3.2.1]oct-2-ene;

(±)-8-methyl-3-[6-(N-pyrrolidinyl)-2-naphthyl]-8-azabicyclo[3.2.1]oct-2-ene;

(±)-8-methyl-3-[6-(N-piperidinyl)-2-naphthyl]-8-azabicyclo[3.2.1]oct-2-ene;

(±)-8-methyl-3-[6-(N-piperazinyl)-2-naphthyl]-8-azabicyclo[3.2.1]oct-2-ene;

(±)-3-[6-(N-homopiperazinyl)-2-naphthyl]-8-methyl-8-azabicyclo[3.2.1]oct-2-ene;

Exo-3-[6-(2-methoxyethoxy)-2-naphthyl]-8-methyl-8-azabicyclo[3.2.1]octane;

Exo-3-[6-methoxy)-2-naphthyl]-8-methyl-8-azabicyclo[3.2.1]octane;

(±)-3-[6-Isoquinolinyl]-8-methyl-8-azabicyclo[3.2.1]oct-2-ene;

(±)-3-[6-Quinolinyl]-8-methyl-8-azabicyclo[3.2.1]oct-2-ene;

(±)-3-[7-Isoquinolinyl]-8-methyl-8-azabicyclo[3.2.1]oct-2-ene;

(±)-3-[7-Quinolinyl]-8-methyl-8-azabicyclo[3.2.1]oct-2-ene;

(±)-3-[1-H-5-Benzimidazolyl]-8-methyl-8-azabicyclo[3.2.1]oct-2-ene;

(±)-3-[1-H-6-Benzimidazolyl]-8-methyl-8-azabicyclo[3.2.1]oct-2-ene;
(±)-3-[1-H-5-Benzotriazolyl]-8-methyl-8-azabicyclo[3.2.1]oct-2-ene;
(±)-3-[1-H-6-Benzotriazolyl]-8-methyl-8-azabicyclo[3.2.1]oct-2-ene;
(±)-3-[2-Amino-1-H-5-benzimidazolyl]-8-methyl-8-azabicyclo[3.2.1]oct-2-ene;
(±)-3-[2-Amino-1-H-6-benzimidazolyl]-8-methyl-8-azabicyclo[3.2.1]oct-2-ene;
(±)-3-[6-Fluoro-2-naphtyl]-8-methyl-8-azabicyclo[3.2.1]oct-2-ene;
(±)-3-[6-Chloro-2-naphtyl]-8-methyl-8-azabicyclo[3.2.1]oct-2-ene;
(±)-3-[6-Iodo-2-naphtyl]-8-methyl-8-azabicyclo[3.2.1]oct-2-ene;
(±)-3-[7-Bromo-2-naphtyl]-8-methyl-8-azabicyclo[3.2.1]oct-2-ene;
(±)-3-[7-Fluoro-2-naphtyl]-8-methyl-8-azabicyclo[3.2.1]oct-2-ene;
(±)-3-[7-Chloro-2-naphtyl]-8-methyl-8-azabicyclo[3.2.1]oct-2-ene;
(±)-3-[7-Iodo-2-naphtyl]-8-methyl-8-azabicyclo[3.2.1]oct-2-ene;
(±)-3-[6-phthalazinyl]-8-methyl-8-azabicyclo[3.2.1]oct-2-ene;
(±)-3-[5-Benzofuranyl]-8-methyl-8-azabicyclo[3.2.1]oct-2-ene;
(±)-3-[6-Benzofuranyl]-8-methyl-8-azabicyclo[3.2.1]oct-2-ene;
(±)-3-[5-Benzothienyl]-8-methyl-8-azabicyclo[3.2.1]oct-2-ene;
(±)-3-[6-Benzothienyl]-8-methyl-8-azabicyclo[3.2.1]oct-2-ene;
(±)-3-[5-Benzothiazolyl]-8-methyl-8-azabicyclo[3.2.1]oct-2-ene;
(±)-3-[6-Benzothiazolyl]-8-methyl-8-azabicyclo[3.2.1]oct-2-ene;
(±)-3-[1-Methyl-5-indolyl]-8-methyl-8-azabicyclo[3.2.1]oct-2-ene;
(±)-3-[1-Methyl-6-indolyl]-8-methyl-8-azabicyclo[3.2.1]oct-2-ene;
(±)-3-[5-Indolizinyl]-8-methyl-8-azabicyclo[3.2.1]oct-2-ene;
(±)-3-[6-Indolizinyl]-8-methyl-8-azabicyclo[3.2.1]oct-2-ene;
(±)-3-[2-Methyl-5-isoindolyl]-8-methyl-8-azabicyclo[3.2.1]oct-2-ene;
(±)-3-[2-Methyl-6-isoindolyl]-8-methyl-8-azabicyclo[3.2.1]oct-2-ene;
(±)-3-[1-Methyl-5-indazolyl]-8-methyl-8-azabicyclo[3.2.1]oct-2-ene;
(±)-3-[1-Methyl-6-indazolyl]-8-methyl-8-azabicyclo[3.2.1]oct-2-ene;
(±)-3-[6-Quinolizinyl]-8-methyl-8-azabicyclo[3.2.1]oct-2-ene;
(±)-3-[7-Quinolizinyl]-8-methyl-8-azabicyclo[3.2.1]oct-2-ene;
(±)-3-[6-Cinnolinyl]-8-methyl-8-azabicyclo[3.2.1]oct-2-ene;
(±)-3-[7-Cinnolinyl]-8-methyl-8-azabicyclo[3.2.1]oct-2-ene;
(±)-3-[6-Quinoxalinyl]-8-methyl-8-azabicyclo[3.2.1]oct-2-ene; or
(±)-3-[7-Quinoxalinyl]-8-methyl-8-azabicyclo[3.2.1]oct-2-ene;

in their labelled or unlabelled form;
or a pharmaceutically acceptable addition salt thereof.

In another embodiment preferred embodiment the compound of the invention represented by the general formula (I) wherein
$R^1$ represents a monocyclic 5- or 6-membered heterocyclic group, which heterocyclic group may be un-saturated, partially un-saturated or saturated, and may contain one or two heteroatoms selected from the group consisting of N, S, O and Se.

In a more preferred embodiment the compound of the invention is represented by the general formula (I) wherein
$R^1$ represents a 5-membered heterocyclic group selected from the group consisting of dioxolanyl, furanyl, furazanyl, imidazolyl, isoimidazolyl, isopyrrolyl, isothiazolyl, isoxazolyl, oxazolyl, pyrazolyl, pyrrolyl, pyrrolidinyl, selenophene-yl, thiadiazolyl, thiazolyl, thienyl, and triazolyl.

In a yet more preferred embodiment the compound of the invention is represented by the general formula (I) wherein
$R^1$ represents a 5-membered heterocyclic group selected from the group consisting of 2-furanyl, 2-thienyl, 4-thiazolyl, 5-imidazolyl, 5-triazolyl, 2-pyrrolyl, 2-selenophene-yl, 3-thiadiazolyl, 5-isoxazolyl, 5-oxazolyl, 5-pyrazolyl, 5-isothiazolyl, 5-furazanyl; which heterocyclic groups may be substituted one or more times with substituents selected from the group consisting halogen, amino, hydroxy, alkoxy, alkoxy-alkoxy, alkoxy-alkyl, sulfanyl, alkylsulfanyl, alkylsulfanyl-alkoxy, alkoxy-alkylsulfanyl, and alkylsulfanyl-alkylsulfanyl.

In an even more preferred embodiment the compound of the invention is represented by the general formula (I) wherein
$R^1$ represents a 6-membered heterocyclic group selected from the group consisting of dioxanyl, morpholinyl, oxazinyl, piperazinyl, piperidinyl, pyranyl, pyrazinyl, pyridazinyl, pyridinyl, and pyrimidinyl.

In a still more preferred embodiment the compound of the invention is represented by the general formula (I) wherein
$R^1$ represents a 6-membered heterocyclic group selected from the group consisting of 3-pyridyl, 4-pyridazyl, 4-pyrimidyl, and 3-pyrazinyl; which heterocyclic groups may be substituted one or more times with substituents selected from the group consisting halogen, amino, hydroxy, alkoxy, alkoxy-alkoxy, alkoxy-alkyl, sulfanyl, alkylsulfanyl, alkylsulfanyl-alkoxy, alkoxy-alkylsulfanyl, and alkylsulfanyl-alkylsulfanyl.

In an even more preferred embodiment the compound of the invention is represented by the general formula (I) wherein
$R^1$ represents a bi-cyclic heterocyclic group selected from the group consisting of 5 or 6-benzimidazolyl, 5 or 6-benzofuranyl, 5 or 6-benzothiazolyl, 5 or 6-benzothienyl, 5 or 6-benzotriazolyl, 6 or 7-cinnolinyl, 5 or 6-indazolyl, 5 or 6-indolizinyl, 5 or 6-indolyl, 5 or 6-isoindolyl, 6 or 7-isoquinolinyl, 6-phthalazinyl, 6 or 7-quinolinyl, 6 or 7-quinolizinyl, and 6 or 7-quinoxalinyl; which heterocyclic groups may be substituted one or more times with substituents selected from the group consisting halogen, amino, hydroxy, alkoxy, alkoxy-alkyl, alkoxy-alkoxy, sulfanyl, alkylsulfanyl, alkylsulfanyl-alkoxy, alkoxy-alkylsulfanyl, and alkylsulfanyl-alkylsulfanyl.

In a most preferred embodiment the compound of the invention is
(±)-3-[2-(3-Bromofuranyl)]-8-H-8-azabicyclo[3.2.1]oct-2-ene;
(±)-3-[2-(3-Bromofuranyl)]-8-methyl-8-azabicyclo[3.2.1]oct-2-ene;

(±)-3-[2-(3-Bromofuranyl)]-8-ethyl-8-azabicyclo[3.2.1]oct-2-ene;
(±)-3-[2-(3-Chlorofuranyl)]-8-methyl-8-azabicyclo[3.2.1]oct-2-ene;
(±)-3-[2-(3-Iodofuranyl)]-8-methyl-8-azabicyclo[3.2.1]oct-2-ene;
(±)-3-[2-(3-Bromothienyl)]-8-methyl-8-azabicyclo[3.2.1]oct-2-ene;
(±)-3-[2-(3-Bromothienyl)]-8-ethyl-8-azabicyclo[3.2.1]oct-2-ene;
(±)-3-[2-(3-Bromothienyl)]-8-H-8-azabicyclo[3.2.1]oct-2-ene;
(±)-3-[2-(3-Iodoothienyl)]-8-methyl-8-azabicyclo[3.2.1]oct-2-ene;
(±)-3-[2-(3,4-Dibromothienyl)]-8-methyl-8-azabicyclo[3.2.1]oct-2-ene;
(±)-3-[2-(3,4-Dichlorothienyl)]-8-methyl-8-azabicyclo[3.2.1]oct-2-ene;
(±)-3-[4-(5-Bromothiazolyl)]-8-methyl-8-azabicyclo[3.2.1]oct-2-ene;
(±)-3-[4-(5-Chlorothiazolyl)]-8-methyl-8-azabicyclo[3.2.1]oct-2-ene;
(±)-3-[4-(5-Iodothiazolyl)]-8-methyl-8-azabicyclo[3.2.1]oct-2-ene;
(±)-3-[5-(4-Bromo-1-methyl-imidazolyl)]-8-methyl-8-azabicyclo[3.2.1]oct-2-ene;
(±)-3-[5-(4-Chloro-1-methyl-imidazolyl)]-8-methyl-8-azabicyclo[3.2.1]oct-2-ene;
(±)-3-[5-(4-Iodo-1-methyl-imidzolyl)]-8-methyl-8-azabicyclo[3.2.1]oct-2-ene;
(±)-3-[5-(4-Bromo-1-methyl-1,2,3-triazolyl)]-8-methyl-8-azabicyclo[3.2.1]oct-2-ene;
(±)-3-[5-(4-Chloro-1-methyl-1,2,3-triazolyl)]-8-methyl-8-azabicyclo[3.2.1]oct-2-ene;
(±)-3-[5-(4-Iodo-1-methyl-1,2,3-triazolyl)]-8-methyl-8-azabicyclo[3.2.1]oct-2-ene;
(±)-3-[2-(3-Bromo-1-methyl-pyrrolyl)]-8-methyl-8-azabicyclo[3.2.1]oct-2-ene;
(±)-3-[2-(3-Chloro-1-methyl-pyrrolyl)]-8-methyl-8-azabicyclo[3.2.1]oct-2-ene;
(±)-3-[2-(3-Iodo-1-methyl-pyrrolyl)]-8-methyl-8-azabicyclo[3.2.1]oct-2-ene;
(±)-3-[2-(3-Bromoselenophenyl)]-8-methyl-8-azabicyclo[3.2.1]oct-2-ene;
(±)-3-[2-(3-Chloroselenophenyl)]-8-methyl-8-azabicyclo[3.2.1]oct-2-ene;
(±)-3-[2-(3-Iodoselenophenyl)]-8-methyl-8-azabicyclo[3.2.1]oct-2-ene;
(±)-3-[3-(4-Bromo-1-2-5-thiadiazolyl)]-8-methyl-8-azabicyclo[3.2.1]oct-2-ene;
(±)-3-[3-(4-Chloro-1-2-5-thiadiazolyl)]-8-methyl-8-azabicyclo[3.2.1]oct-2-ene;
(±)-3-[3-(4-Iodo-1-2-5-thiadiazolyl)]-8-methyl-8-azabicyclo[3.2.1]oct-2-ene;
(±)-3-[5-(4-Bromo-isoxazolyl)]-8-methyl-8-azabicyclo[3.2.1]oct-2-ene;
(±)-3-[5-(4-Chloro-isoxazolyl)]-8-methyl-8-azabicyclo[3.2.1]oct-2-ene;
(±)-3-[5-(4-Iodo-isoxazolyl)]-8-methyl-8-azabicyclo[3.2.1]oct-2-ene;
(±)-3-[5-(4-Bromo-oxazolyl)]-8-methyl-8-azabicyclo[3.2.1]oct-2-ene;
(±)-3-[5-(4-Chloro-oxazolyl)]-8-methyl-8-azabicyclo[3.2.1]oct-2-ene;
(±)-3-[5-(4-Iodo-oxazolyl)]-8-methyl-8-azabicyclo[3.2.1]oct-2-ene;
(±)-3-[5-(4-Bromo-1-methylpyrazolyl)]-8-methyl-8-azabicyclo[3.2.1]oct-2-ene;
(±)-3-[5-(4-Chloro-1-methylpyrazolyl)]-8-methyl-8-azabicyclo[3.2.1]oct-2-ene;
(±)-3-[5-(4-Iodo-1-methylpyrazolyl)]-8-methyl-8-azabicyclo[3.2.1]oct-2-ene;
(±)-3-[5-(4-Bromo-isothiazolyl)]-8-methyl-8-azabicyclo[3.2.1]oct-2-ene;
(±)-3-[5-(4-Chloro-isothiazolyl)]-8-methyl-8-azabicyclo[3.2.1]oct-2-ene;
(±)-3-[5-(4-Iodo-isothiazolyl)]-8-methyl-8-azabicyclo[3.2.1]oct-2-ene;
(±)-3-[5-(4-Bromo-furazanyl)]-8-methyl-8-azabicyclo[3.2.1]oct-2-ene;
(±)-3-[5-(4-Chloro-furazanyl)]-8-methyl-8-azabicyclo[3.2.1]oct-2-ene;
(±)-3-[5-(4-Iodo-furazanyl)]-8-methyl-8-azabicyclo[3.2.1]oct-2-ene;
(±)-3-[3-(2-Bromo-pyridyl)]-8-methyl-8-azabicyclo[3.2.1]oct-2-ene;
(±)-3-[3-(2-Chloro-pyridyl)]-8-methyl-8-azabicyclo[3.2.1]oct-2-ene;
(±)-3-[3-(4-Bromo-pyridyl)]-8-methyl-8-azabicyclo[3.2.1]oct-2-ene;
(±)-3-[3-(4-Chloro-pyridyl)]-8-methyl-8-azabicyclo[3.2.1]oct-2-ene;
(±)-3-[4-(3-Bromo-pyridazyl)]-8-methyl-8-azabicyclo[3.2.1]oct-2-ene;
(±)-3-[4-(3-Chloro-pyridazyl)]-8-methyl-8-azabicyclo[3.2.1]oct-2-ene;
(±)-3-[4-(3,6-Dibromo-pyridazyl)]-8-methyl-8-azabicyclo[3.2.1]oct-2-ene;
(±)-3-[4-(3,6-Dichloro-pyridazyl)]-8-methyl-8-azabicyclo[3.2.1]oct-2-ene;
(±)-3-[4-(5-Bromo-pyrimidyl)]-8-methyl-8-azabicyclo[3.2.1]oct-2-ene;
(±)-3-[4-(5-Chloro-pyrimidyl)]-8-methyl-8-azabicyclo[3.2.1]oct-2-ene;
(±)-3-[3-(2,6-dichloropyrazinyl)]-8-methyl-8-azabicyclo[3.2.1]oct-2-ene; or
(±)-3-[3-(2-Chloro-pyrazinyl)]-8-methyl-8-azabicyclo[3.2.1]oct-2-ene;
in labelled or unlabelled form;
or a pharmaceutically acceptable addition salt thereof.

Definition of Substituents

In the context of this invention halogen represents a fluorine, a chlorine, a bromine or an iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention an alkoxy-alkyl group designates an "alkyl-O-alkyl-" group, wherein alkyl is as defined above.

In the context of this invention an alkoxy-alkoxy group designates an "alkyl-O-alkyl-O—" group, wherein alkyl is as defined above.

In the context of this invention an alkylsulfanyl designates an "alkyl-S—" group (a thio-alkoxy group), wherein alkyl is as defined above. Likewise alkylsulfanyl-alkoxy, alkoxy-alkylsulfanyl, and alkylsulfanyl-alkylsulfanyl designates an alkylsulfanyl as defined above, attached to another alkylsulfanyl or to an alkoxy group as defined above.

In the context of this invention an alkylcarbonyloxy group designates an "alkyl-CO—O—" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono- or polycyclic aryl group designates a monocyclic or polycyclic aromatic hydrocarbon group. Examples of preferred aryl groups of the invention include phenyl, naphthyl and anthracenyl.

In the context of this invention an aralkyl group designates a mono- or polycyclic aryl group as defined above, which aryl group is attached to an alkyl group as also defined above. A preferred aralkyl group of the invention is benzyl.

In the context of this invention an aryloxy group designates an "aryl-O—" group, wherein aryl is a mono- or polycyclic aryl group as defined above.

In the context of this invention a fluorescent group is a functional group which can be detected by spectroscopic methods and may be selected from the group of naturally occurring fluorophores or chemically synthesized fluorescent groups, such as rhodamine, green fluorescent protein or fluorescein and its derivatives.

In the context of this invention a monocyclic 5- or 6-membered heterocyclic group is a monocyclic compound holding one or more heteroatoms in its ring structure. Preferred heteroatoms include nitrogen (N), oxygen (O), sulphur (S) and selen (Se). The ring structure may in particular be aromatic (i.e. a heteroaryl), unsaturated or partially unsaturated.

Examples of preferred heterocyclic aromatic monocyclic groups of the invention include 1,3,2,4- or 1,3,4,5-dioxadiazolyl, dioxatriazinyl, dioxazinyl, 1,2,3-, 1,2,4-, 1,3,2- or 1,3,4-dioxazolyl, 1,3,2,4- or 1,3,4,5-dithiadiazolyl, dithiatriazinyl, dithiazinyl, 1,2,3-dithiazolyl, 2- or 3-furanyl, furazanyl, 1,2 or 4-imidazolyl, isoindazolyl, isothiazol-3,4 or 5-yl, isoxazol-3,4 or 5-yl, 1,2,3-, 1,2,4-, 1,2,5- or 1,3,4-oxadiazol-3,4 or 5-yl, oxatetrazinyl, oxatriazinyl, 1,2,3,4- or 1,2,3,5-oxatriazolyl, oxazol-2,4 or 5-yl, 2 or 3-pyrazinyl, 1,3 or 4-pyrazolyl, 3 or 4-pyridazinyl, 2,3 or 4-pyridinyl, 2,4 or 5-pyrimidinyl, 1,2 or 3-pyrrolyl (azolyl), 1,2,3,4- or 2,1,3,4-tetrazolyl, thiadiazol-3,4 or 5-yl, thiazol-2,4 or 5-yl, 2 or 3-thienyl, 1,2,3-, 1,2,4- or 1,3,5-triazinyl, and 1,2,3-, 1,2,4-, 2,1,3- or 4,1,2-triazolyl.

Examples of preferred saturated or partially saturated heterocyclic monocyclic groups of the invention include 1,3,5,6,2-dioxadiazinyl, 1,2,3,4,5-, 1,2,3,5,4-dioxadiazolyl, dioxanyl, 1,3-dioxolyl, 1,3,5,6,2-dithiadiazinyl, 1,2,3,4,5- or 1,2,3,5,4-dithiadiazolyl, 2-isoimidazolyl, isopyrrolyl, isotetrazolyl, 1,2,3- or 1,2,4-isotriazolyl, morpholinyl, oxadiazinyl, 1,2,4-, 1,2,6-, 1,3,2-, 1,3,6- or 1,4,2-oxazinyl, piperazinyl, homopiperazinyl, piperidinyl, 1,2-, 1,3- or 1,4-pyranyl, and 1,2,3-pyrrolidinyl.

In the context of this invention a bicyclic heteroaryl group composed of a 5 to 6 membered monocyclic heteroaryl group and a fused benzene ring or another 5 to 6 membered monocyclic heteroaryl group designates a monocyclic 5 to 6 membered heteroaryl group as defined above, which group is fused to a benzene ring or fused to another 5 to 6 membered heteroaryl group as defined above.

Examples of preferred bicyclic heteroaryl groups of the invention include 3,4,5,6 or 7-anthranilyl, 2,4,5 or 6-benzimidazolyl, 1,3-benzisodiazol-2,4,5,6 or 7-yl, 1,2-benzisothianin-3,4,5,6,7 or 8-yl, 1,4-benzisothiazin-2,3,5,6,7 or 8-yl, 2,3,4,5,6 or 7-benzofuranyl, 2,3,4,5,6,7 or 8-benzopyranyl, 1,3,2-, 1,4,2-, 2,3,1- or 3,1,4-benzoxazinyl, 2,3,4,5,6 or 7-benzofuranyl, 1,3,4,5,6 or 7-isobenzofuranyl, 1,2- or 1,4-benzopyranyl, 2,4,5,6 or 7-benzothiazolyl, 5 or 6-benzothienyl, 5 or 6-benzotriazolyl, 2,3,4,5,6,7 or 8-chromanyl, 4H-chromenyl, 3,4,5,6,7 or 8-cinnolinyl, 2,3,4,5,6 or 7-indanyl, 3,4,5,6 or 7-indazolyl, 5 or 6-indolizinyl, 2,3,4,5,6 or 7-indolyl, 1,3,4,5,6 or 7-isoindolyl, 2,3,4,5,6,7 or 8-quinolinyl, 1,3,4,5,6,7 or 8-isoquinolinyl, 1,4,5,6,7 or 8-phthalazinyl, thieno[3.2-b]thienyl, and thieno[2.3-b]thienyl, 1,4,5,6,7,8-phthalazinyl, 2,4,5,6,7,8-quinazolinyl, 6 or 7-quinolinyl, 6 or 7-quinolizinyl, and 2,3,5,6,7,8-quinoxalinyl.

The compounds of the invention may be labelled or unlabelled. In their labelled form they may be labelled by incorporation of a isotope into the molecule. In the context of this invention an isotope of a compound means that one or more atom in the compound is substituted with an isotope of the naturally occurring atoms including deuterium, tritium, $^{13}C$, $^{14}C$, $^{131}I$, $^{125}I$, $^{123}I$, and $^{18}F$. The isotope incorporation may be measured by conventional scintillation counting techniques.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulfonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Method of Producing the Compounds

The compounds of the invention may be prepared by any conventional method useful for the preparation of analogous compounds and as described in the examples below.

Starting materials for the processes described in the present patent application are known or can be prepared by known processes from commercially available materials.

A compound of the invention can be converted to another compound of the invention using conventional methods.

In a preferred embodiment, the compounds of the invention may be prepared the following method, which method comprises:

A) the step of reacting a compound having the formula

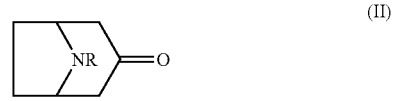

(II)

wherein R is as defined herein,
with a compound of the formula $R^1$—Li,
wherein $R^1$ is as defined herein,
followed by dehydration of the compound obtained; or B) the step of reacting a compound having the formula

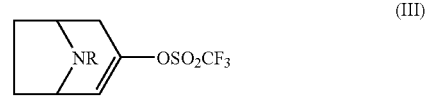

(III)

wherein R is as defined herein,
with a compound of formula $R^1$—X,
wherein $R^1$ is as defined herein,
and X represents halogen, boronic acid, or trialkylstannyl; or C) the step of reducing a compound having the formula

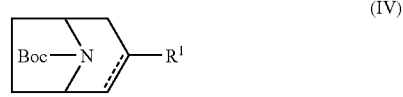

(IV)

wherein $R^1$ is as defined herein.

The products of the reactions described herein are isolated by conventional means such as extraction, crystallisation, distillation, chromatography, and the like.

Biological Activity

The compounds of the present invention have proven to be nicotinic receptor modulators. In the context of this invention the term "modulator" covers agonists, partial agonists, antagonists and allosteric modulators of the nicotinic acetyl choline receptor (nAChR).

The compounds of the present invention exhibit a nicotinic pharmacology at least as good as nicotine itself, but preferably with lesser or even without the side effects associated with the use of nicotine. Moreover, the compounds of the invention are believed to have the potential as enhancers of neurotransmitter secretion, and suppress symptoms associated with a low activity of neurotransmitters.

The compounds of the present invention may in particular be characterised by having one or more of the following functionalities: A high binding selectivity for the receptor subtypes of neuronal nAChR's, in particular the α3 and/or the α7 subtype, binding selectivity for the serotonin receptor, a low affinity for the muscular subtype, an induction of cell survival, an oral efficacy in vivo of arousal/attention, a low toxicity in vivo, and by being non-mutagenic.

Due to their pharmacological profile the compounds of the invention may be useful for the treatment of diseases or conditions as diverse as CNS related diseases, diseases related to smooth muscle contraction, endocrine disorders, diseases related to neurodegeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourettes syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, pre-menstrual syndrome, late luteal phase syndrome, chronic fatigue syndrome, mutism, trichotillomania, and jetlag.

In another preferred embodiment the compounds of the invention may be useful for the treatment of diseases, disorders, or conditions associated with smooth muscle contractions, including convulsive disorders, angina pectoris, premature labor, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neurodegeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative collitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepin-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylaxis and alleviation of withdrawal symptoms and abstinence as well as treatment resulting in a voluntary diminished intake of the addictive substance.

Neuroimaging

The 8-azabicyclo[3.2.1]oct-2-ene and -octane derivatives of the invention, in particular those being selective for the nicotinic receptor subtype α3, may be useful as diagnostic tools or monitoring agents in various diagnostic methods, and in particular for in vivo receptor imaging (neuroimaging).

In another aspect of the invention a method for the non-invasive determination of the distribution of a tracer compound inside a whole, intact living animal or human body using a physical detection method is provided. According to this method a tracer compound is a compound of the invention, or any of its enantiomers or any mixture thereof, or a pharmaceutically acceptable salt thereof, in labelled or unlabelled form.

In a preferred embodiment the physical detection method is selected from PET, SPECT; MRS, MRI, CAT, or combinations thereof.

The compounds of the invention may be used in their labelled or unlabelled form. In the context of this invention "label" stands for the binding of a marker to the compound of interest that will allow easy quantitative detection of said compound.

The labelled compound of the invention preferably contains at least one radionuclide as a label. Positron emitting radionuclides are all candidates for usage. In the context of this invention the radionuclide is preferably selected from $^{11}C$, $^{18}F$, $^{15}O$, $^{13}N$, $^{123}I$, $^{125}I$, $^{131}I$, $^{3}H$ and $^{99m}Tc$.

An examples of commercially available labelling agents, which can be used in the preparation of the labelled compounds of the present invention is $[^{11}C]O_2$, $^{18}F$, and NaI with different isotopes of Iodine.

In particular $[C^{11}]O_2$ may be converted to a $[^{11}C]$-methylating agent, such as $[C^{11}]H_3I$ or $[C^{11}]$-methyl triflate.

Labelled compounds containing e.g. $[^{125}I]$ labelled 1-iodoprop-1-en-3-yl as substituent on N-8 may be prepared as described in the art [Elmaleh, et al.; *J. Nucl. Med.* 1996 37 1197–1202].

Labelled compounds containing e.g. $[^{18}F]$-alkyl substituted N-8 may be prepared as described in the art, e.g. in WO 96/39198.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including deuterium, tritium, $^{13}C$, $^{14}C$, $^{131}I$, $^{125}I$, $^{131}I$, and $^{18}F$, the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diagnostically effective amount of the labelled or unlabelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers and/or diluents.

In a preferred embodiment, the invention provides pharmaceutical compositions comprising the chemical compound of the invention, or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical compositions of the invention may be those suitable for oral, rectal, nasal, topical (including buccal and sub-lingual), transdermal, vaginal or parenteral (including intramuscular, sub-cutaneous and intravenous) administration, or those in a form suitable for administration by inhalation or insufflation.

The chemical compound of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

The dose administered must of course be carefully adjusted to the age, weight and condition of the individual being treated, as well as the route of administration, dosage form and regimen, and the result desired. It is presently contemplated that compositions containing of from about 0.1 to about 500 mg of active ingredient per unit dosage, preferably of from about 1 to about 100 mg, most preferred of from about 1 to about 10 mg, are suitable for therapeutic treatments.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

Methods of Therapy

The compounds of the present invention are valuable nicotinic ACh receptor modulators and therefore useful for the treatment of a range of ailments involving cholinergic dysfunction as well as a range of disorders responsive to the action of nicotinic ACh receptor modulators as well as the serotonin receptor.

In another aspect the invention relates to the a method of the treatment or alleviation of a disease, disorder or condition of a living animal body, including a human, which disease, disorder or condition is responsive to the action of a nicotinic Acetyl Choline Receptor (nAChR) modulator, which method comprises the step of administering to such a living animal body, including a human, in need thereof a therapeutically effective amount of the chemical compound of the invention.

In the context of this invention the term "treating" covers treatment, prevention, prophylaxis or alleviation, and the term "disease" covers illnesses, diseases, disorders and conditions related to the disease in question.

In a preferred embodiment the disease or disorder to be treated is a disease or disorder of the central nervous system, a disease or disorder caused by or related to smooth muscle contraction, an endocrine disorder, a disease or disorder caused by or related to neuro-degeneration, a disease or disorder caused by or related to inflammation, pain, a withdrawal symptom caused by the termination of abuse of chemical substances.

In a more preferred embodiment the disease or disorder of the central nervous system is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourettes syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, pre-menstrual syndrome, late luteal phase syndrome, chronic fatigue syndrome, mutism, trichotillomania, and jetlag In another preferred embodiment the disease or disorder caused by or related to smooth muscle contraction is convulsive disorders, angina pectoris, premature labor, convulsions, diarrhoea, asthma, epilepsy, tardive dyskinesia, hyperkinesia, premature ejaculation, and erectile difficulty.

In a third preferred embodiment the endocrine disorder is thyrotoxicosis, pheochromocytoma, hypertension and arrhythmias.

In a fourth preferred embodiment the neuro-degenerative disease is transient anoxia and induced neurodegeneration.

In a fifth preferred embodiment the disease or disorder caused by or related to inflammation is an inflammatory skin disorder such as acne and rosacea, Chron's disease, inflammatory bowel disease, ulcerative collitis, and diarrhoea.

In a sixth preferred embodiment pain is a mild, a moderate or a severe pain of acute, chronic or recurrent character, a pain caused by migraine, a postoperative pain, or a phantom limb pain.

In a third preferred embodiment the addictive substance is a nicotine containing product such as tobacco, an opioids such as heroin, cocaine or morphine, a benzodiazepine or a benzodiazepin-like drug, or alcohol.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples which are not intended to be in any way limiting to the scope of the invention as claimed.

Example 1

Preparatory Example

General: All reactions involving air sensitive reagents or intermediates were performed under nitrogen and in anhydrous solvents. Magnesium sulfate was used as drying agent in the workup-procedures and solvents were evaporated under reduced pressure.

(±)-3-[6-(Methoxy)-2-naphthyl]-8-methyl-8-azabicyclo[3.2.1]oct-2-ene fumaric acid salt: To a solution of 2-Bromo-6-methoxynaphthalene (8.8 g, 37.1 mmol) in tetrahydrofuran (150 ml) was added: buthyllithium (17.0 ml, 40.8 mmol) at −70° C. The mixture was stirred for 1 h at −70° C., followed by addition of tropinone (5.2 g, 37.1 mmol) in tetrahydrofuran (75 ml). The mixture was stirred at −70° C. for 30 min, and was allowed to reach −20° C. Aqueous sodium hydroxide (200 m, 1 M) was added at −20° C., and the mixture was allowed to reach room temperature. The mixture was extracted two times with diethyl ether (50 ml). The mixture was recrystalised from petroleum ether and yielded the intermediate product endo and exo-3-hydroxy-3-[6-(methoxy)-2-naphtyl]-8-methyl-8-azabicyclo[3.2.1]octane. Yield 4.06 g, 37%.

A mixture of endo and exo-3-hydroxy-3-[6-(methoxy)-2-naphthyl]-8-methyl-8-azabicyclo[3.2.1]octane (2.50 g, 8.4 mmol), thionyl chloride (12.5 g, 105 mmol) and tetrahydrofuran (50 ml) was stirred for 30 min at 50° C. The excess of thionyl chloride was evaporated. Potassium hydroxide (3.8 g, 67.2 mmol) and ethanol (60 ml) were added, and the mixture stirred for 20 min. The crude mixture was purified by chromatography on silica gel with dichloromethane, methanol and conc. ammonia (89:10:1) gave the title compound as free base. The corresponding salt was obtained by addition of a diethyl ether and methanol mixture (9:1), saturated with fumaric acid. Yield 2.0 g, 60%. Mp 192.6–195.4° C.

(±)-3-[6-(Hydroxy)-2-naphthyl]-8-methyl-8-azabicyclo[3.2.1]oct-2-ene fumaric acid salt:

To a solution of 2-bromo-6-methoxymethoxynaphthalene (8.3 g, 28.5 mmol) in tetrahydrofuran (100 ml) was added: buthyllithium (12.5 ml, 31.3 mmol) at −70° C. The mixture was stirred for 1 h at −70° C., followed by addition of tropinone (3.9 g, 28.5 mmol) in tetrahydrofuran (50 ml). The mixture was stirred at −70° C. for 30 min and was allowed to reach −20° C. Aqueous sodium hydroxide (75 ml, 1 M) was added at −20° C., and the mixture was allowed to reach room temperature. The mixture was extracted two times with diethyl ether (75 ml). The mixture was triturated with petroleum ether, and yielded the intermediate product endo and exo-3-hydroxy-3-[6-(methoxymethoxy)-2-naphthyl]-8-methyl-8-azabicyclo[3.2.1]octane. Yield 4.9 g, 53%.

A mixture of endo and exo-3-hydroxy-3-[6-(methoxymethoxy)-2-naphtyl]-8-methyl-8-azabicyclo[3.2.1]octane (2.70 g, 7.9 mmol), thionyl chloride (11.8 g, 98.8 mmol) and tetrahydrofuran (50 ml) was stirred for 30 min at 50° C. The excess of thionyl chloride was evaporated. Potassium hydroxide (3.5 g, 63.2 mmol) and ethanol (75 ml) were added, and the mixture stirred for 30 min. The crude mixture was purified by chromatography on silica gel with dichloromethane, methanol and conc. ammonia (89:10:1), and gave the title compound as free base. The corresponding salt was obtained by addition of a diethyl ether and methanol mixture (9:1) saturated with fumaric acid. Yield 1.4 g, 60%. Mp 191.2–194.7° C.

(±)-3-[6-(2-Methoxyethoxy)-2-naphthyl]-8-methyl-8-azabicyclo[3.2.1]oct-2-ene fumaric acid salt: To a solution of 2-bromo-6-(2-methoxyethoxy)naphthalene (8.0 g, 28.5 mmol) in tetrahydrofuran (100 ml) was added: buthyllithium (12.5 ml, 31.3 mmol) at −70° C. The mixture was stirred for 1 h at −70° C. followed by addition of tropinone (3.9 g, 28.5 mmol) in tetrahydrofuran (100 ml). The mixture was stirred at −70° C. for 30 min and was allowed to reach room temperature overnight. Aqueous sodium hydroxide (100 ml, 1M) was added. The mixture was extracted two times with diethyl ether (100 ml). The crude mixture was purified by chromatography on silica gel with dichloromethane, methanol and conc. ammonia (89:10:1), and gave endo and exo-3-hydroxy-3-[6-(2-methoxyethoxy)-2-naphthyl]-8-methyl-8-azabicyclo[3.2.1]octane. Yield 1.44g, 15%.

A mixture of endo and exo-3-hydroxy-3-[6-(2-methoxyethoxy)-2-naphthyl]-8-methyl-8-azabicyclo[3.2.1]octane (1.3 g, 3.8 mmol), thionyl chloride (5.7 g, 47.6 mmol) and tetrahydrofuran (100 ml) was stirred for 30 min at 50° C. The excess of thionyl chloride was evaporated. Potassium hydroxide (1.7 g, 30.4 mmol) and ethanol (20 ml) were added and the mixture stirred for 20 min. The crude mixture was purified by chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Yield 0.25 g, 15%. Mp 157.3–158.9° C.

Exo-3-[6-(methoxymethoxy)-2-naphthyl]-8-methyl-8-azabicyclo[3.2.1]octane fumaric acid salt: A mixture of endo and exo-3-hydroxy-3-[6-(methoxymethoxy)-2-naphthyl] -8-methyl-8-azabicyclo[3.2.1]octane (1.0 g, 3.1 mmol), Raney nickel (20 g, 50% in water) and ethanol (50 ml) was stirred overnight. The ethanol was separated, and the Raney nickel was extracted two times with ethanol (25 ml). The crude mixture was purified by chromatography on silica gel with dichloromethane, methanol and conc. ammonia (89: 10:1) gave the title compound. The corresponding salt was obtained by addition of a diethyl ether and methanol mixture (9:1) saturated with fumaric acid. Yield 20 mg, 1.5%. Mp 126.5–129.6° C.

(±)-3-[6-(Acetyloxy)-2-naphthyl]-8-methyl-8-azabicyclo[3.2.1]oct-2-ene fumaric acid salt: A mixture of (±)-3-[6-(hydroxy)-2-naphthyl]-8-methyl-8-azabicyclo[3.2.1]oct-2-ene (0.49 mg, 1.8 mmol), acetic acid anhydride (1.9 g, 18 mmol) and dichloromethane (20 ml) was stirred at reflux for 1.5 h. The mixture was evaporated and aqueous sodiumhydroxide (1 M, 50 ml) was added followed by extraction with ethyl acetate (2×25 ml). The corresponding salt was obtained by addition of a diethyl ether and methanol mixture (9:1) saturated with fumaric acid. Yield 380 mg, 50%. Mp 154.2–155.6° C.

The following compounds are prepared likewise:

(±)-8-Methyl-3-[6-(thioethoxy)-2-naphtyl]-8-azabicyclo[3.2.1]oct-2-ene;
(±)-8-Methyl-3-[6-(thiomethoxy)-2-naphtyl]-8-azabicyclo[3.2.1]oct-2-ene;
(±)-3-[6-(Ethoxy)-2-naphtyl]-8-methyl-8-azabicyclo[3.2.1]oct-2-ene;
(±)-3-[6-(Mercapto)-2-naphtyl]-8-methyl-8-azabicyclo[3.2.1]oct-2-ene;
(±)-3-[6-(2-Methoxythioethoxy)-2-naphtyl]-8-methyl-8-azabicyclo[3.2.1]oct-2-ene;
(±)-3-[6-(2-Ethoxyethoxy)-2-naphtyl]-8-methyl-8-azabicyclo[3.2.1]oct-2-ene;
(±)-3-[6-Bromo-2-naphtyl]-8-methyl-8-azabicyclo[3.2.1]oct-2-ene;
(±)-3-[6-Amino-2-naphtyl]-8-methyl-8-azabicyclo[3.2.1]oct-2-ene;
(±)-3-[6-Dimethylamino-2-naphtyl]-8-methyl-8-azabicyclo[3.2.1]oct-2-ene;
(±)-3-[6-Diethylamino-2-naphtyl]-8-methyl-8-azabicyclo[3.2.1]oct-2-ene;
(±)-8-Methyl-3-[6-(N-pyrrolidinyl)-2-naphtyl]-8-azabicyclo[3.2.1]oct-2-ene;
(±)-8-Methyl-3-[6-(N-piperidinyl)-2-naphtyl]-8-azabicyclo[3.2.1]oct-2-ene;
(±)-8-Methyl-3-[6-(N-piperazinyl)-2-naphtyl]-8-azabicyclo[3.2.1]oct-2-ene;
(±)-3-[6-(N-Homopiperazinyl)-2-naphtyl]-8-methyl-8-azabicyclo[3.2.1]oct-2-ene;
Exo-3-[6-(2-Methoxyethoxy)-2-naphtyl]-8-methyl-8-azabicyclo[3.2.1]octane;
Exo-3-[6-Methoxy)-2-naphtyl]-8-methyl-8-azabicyclo[3.2.1]octane;
(±)-3-[6-Isoquinolinyl]-8-methyl-8-azabicyclo[3.2.1]oct-2-ene;
(±)-3-[6-Quinolinyl]-8-methyl-8-azabicyclo[3.2.1]oct-2-ene;
(±)-3-[7-Isoquinolinyl]-8-methyl-8-azabicyclo[3.2.1]oct-2-ene;
(±)-3-[7-Quinolinyl]-8-methyl-8-azabicyclo[3.2.1]oct-2-ene;
(±)-3-[1-H-5-Benzimidazolyl]-8-methyl-8-azabicyclo[3.2.1]oct-2-ene;
(±)-3-[1-H-6-Benzimidazolyl]-8-methyl-8-azabicyclo[3.2.1]oct-2-ene;
(±)-3-[1-H-5-Benzotriazolyl]-8-methyl-8-azabicyclo[3.2.1]oct-2-ene;
(±)-3-[1-H-6-Benzotriazolyl]-8-methyl-8-azabicyclo[3.2.1]oct-2-ene;
(±)-3-[2-Amino-1-H-5-benzimidazolyl]-8-methyl-8-azabicyclo[3.2.1]oct-2-ene;
(±)-3-[2-Amino-1-H-6-benzimidazolyl]-8-methyl-8-azabicyclo[3.2.1]oct-2-ene;
(±)-3-[6-Fluoro-2-naphtyl]-8-methyl-8-azabicyclo[3.2.1]oct-2-ene;
(±)-3-[6-Chloro-2-naphtyl]-8-methyl-8-azabicyclo[3.2.1]oct-2-ene;
(±)-3-[6-Iodo-2-naphtyl]-8-methyl-8-azabicyclo[3.2.1]oct-2-ene;
(±)-3-[7-Bromo-2-naphtyl]-8-methyl-8-azabicyclo[3.2.1]oct-2-ene;
(±)-3-[7-Fluoro-2-naphtyl]-8-methyl-8-azabicyclo[3.2.1]oct-2-ene;
(±)-3-[7-Chloro-2-naphtyl]-8-methyl-8-azabicyclo[3.2.1]oct-2-ene;
(±)-3-[7-Iodo-2-naphtyl]-8-methyl-8-azabicyclo[3.2.1]oct-2-ene;
(±)-3-[6-phthalazinyl]-8-methyl-8-azabicyclo[3.2.1]oct-2-ene;
(±)-3-[5-Benzofuranyl]-8-methyl-8-azabicyclo[3.2.1]oct-2-ene;
(±)-3-[6-Benzofuranyl]-8-methyl-8-azabicyclo[3.2.1]oct-2-ene;
(±)-3-[5-Benzothienyl]-8-methyl-8-azabicyclo[3.2.1]oct-2-ene;
(±)-3-[6-Benzothienyl]-8-methyl-8-azabicyclo[3.2.1]oct-2-ene;
(±)-3-[5-Benzothiazolyl]-8-methyl-8-azabicyclo[3.2.1]oct-2-ene;
(±)-3-[6-Benzothiazolyl]-8-methyl-8-azabicyclo[3.2.1]oct-2-ene;
(±)-3-[1-Methyl-5-indolyl]-8-methyl-8-azabicyclo[3.2.1]oct-2-ene;
(±)-3-[1-Methyl-6-indolyl]-8-methyl-8-azabicyclo[3.2.1]oct-2-ene;
(±)-3-[5-Indolizinyl]-8-methyl-8-azabicyclo[3.2.1]oct-2-ene;
(±)-3-[6-Indolizinyl]-8-methyl-8-azabicyclo[3.2.1]oct-2-ene;
(±)-3-[2-Methyl-5-isoindolyl]-8-methyl-8-azabicyclo[3.2.1]oct-2-ene;
(±)-3-[2-Methyl-6-isoindolyl]-8-methyl-8-azabicyclo[3.2.1]oct-2-ene;
(±)-3-[1-Methyl-5-indazolyl]-8-methyl-8-azabicyclo[3.2.1]oct-2-ene;
(±)-3-[1-Methyl-6-indazolyl]-8-methyl-8-azabicyclo[3.2.1]oct-2-ene;
(±)-3-[6-Quinolizinyl]-8-methyl-8-azabicyclo[3.2.1]oct-2-ene;
(±)-3-[7-Quinolizinyl]-8-methyl-8-azabicyclo[3.2.1]oct-2-ene;
(±)-3-[6-Cinnolinyl]-8-methyl-8-azabicyclo[3.2.1]oct-2-ene;
(±)-3-[7-Cinnolinyl]-8-methyl-8-azabicyclo[3.2.1]oct-2-ene;
(±)-3-[6-Quinoxalinyl]-8-methyl-8-azabicyclo[3.2.1]oct-2-ene; and
(±)-3-[7-Quinoxalinyl]-8-methyl-8-azabicyclo[3.2.1]oct-2-ene.

Method A (±)-3-[2-(3-Bromothienyl)]-8-methyl-8-azabicyclo[3.2.1]oct-2-ene fumaric acid salt: To a solution of 3-bromothiophene (25.0 g, 153.3 mmol) in THF (250 ml) was added lithiumdiisopropylamide (2 M, 168.7 mmol) at −80° C. The mixture was stirred for 1 h at −80° C. followed by addition of tropinone (21.3 g, 153.3 mmol) in THF (200 ml). The mixture was stirred at −80° C. for 1 h and was allowed to reach roomtemperature overnight. Sodium hydroxide (1 M, 200 ml) was added and extracted three times with diethylether (300 ml). Chromatography on silica gel with dichloromethane, methanol and conc. ammonia (89:10:1) gave the intermediate endo and exo-3-[3-bromo-(2-thienyl)]-3-hydroxy-8-methyl-8-azabicyclo[3.2.1]octane. Yield 8.90 g, 19%.

A mixture of endo and exo-3-[3-bromo-(2-thienyl)]-3-hydroxy-8-methyl-8-azabicyclo[3.2.1]octane (8.85 g, 29.3 mmol) and concentrated hydrochloric acid (100 ml) was stirred for 2 h. The hydrochloric acid was evaporated and sodium hydroxide (1 M, 200 ml) was added and the mixture was extracted twice with ethyl acetate (2×100 ml). Yield 8.3 g, 100%. The corresponding salt was obtained by addition of a diethyl ether and methanol mixture (9:1), saturated with fumaric acid. Mp 130–132° C.

(±)-3-[2-(3-Bromofuranyl)]-8-methyl-8-azabicyclo[3.2.1]oct-2-ene fumaric acid salt: Was prepared according to method A. Mp 150.3–153.0° C.

Method B (±)-3-[2-(3-Bromothienyl)]-8-H-8-azabicyclo[3.2.1]oct-2-ene fumaric acid salt: To a mixture of (±)-3-[2-(3-bromothienyl)]-8-methyl-8-azabicyclo[3.2.1]oct-2-ene (4.0 g, 14.1 mmol) and anhydrous xylene (40 ml) was added: 2-chloroethylchloroformate (3.02 g, 21.1 mmol) at 0° C. The mixture was stirred at reflux for 2 days. Methanol (50 ml) was added and the mixture was heated at reflux for 2 h. The methanol was evaporated and sodium hydroxide (60 ml, 1 M) was added. The mixture was extracted with ethyl acetate (2×50 ml). The crude mixture was purified by chromatography on silica gel with dichloromethane, methanol and conc. ammonia (89:10:1) gave the title compound. Yield 2.96 g, 78%. The corresponding salt was obtained by addition of a diethyl ether and methanol mixture (9:1) saturated with fumaric acid. Mp 184–186° C.

(±)-3-[2-(3-Bromofuranyl)]-8-H-8-azabicyclo[3.2.1]oct-2-ene fumaric acid salt: Was prepared according to method B. Mp 176.1–176.9° C.

Method C (±)-3-[2-(3-Bromothienyl)]-8-ethyl-8-azabicyclo[3.2.1]oct-2-ene fumaric acid salt: A mixture of (±)-3-[2-(3-bromothienyl)]-8-H-8-azabicyclo[3.2.1]oct-2-ene (0.70 g, 2.6 mmol), bromoethane (339 mg, 3.1 mmol), diisopropylethylamine (335 mg, 2.6 mmol) and dimethylformamide (20 ml) was stirred at 80° C. for 4 h. Sodium hydroxide (40 ml, 1 M) was added and the mixture was extracted with ethyl acetate (2×40 ml). The crude mixture was purified by chromatography on silica gel with dichloromethane, methanol and conc. ammonia (89:10:1) gave the title compound. Yield 0.57 g (73%). The corresponding salt was obtained by addition of a diethyl ether and methanol mixture (9:1) saturated with fumaric acid. Mp 136–138° C.

(±)-3-[2-(3-Bromofuranyl)]-8-ethyl-8-azabicyclo[3.2.1]oct-2-ene fumaric acid salt: Was prepared according to method C. Mp 139–141.2° C.

The following compounds are prepared likewise:

(±)-3-[2-(3-Iodothienyl)]-8-methyl-8-azabicyclo[3.2.1]oct-2-ene;
(±)-3-[2-(3-Chlorofuranyl)]-8-methyl-8-azabicyclo[3.2.1]oct-2-ene;
(±)-3-[2-(3-Iodofuranyl)]-8-methyl-8-azabicyclo[3.2.1]oct-2-ene;
(±)-3-[1-(2-Iodophenyl)]-8-methyl-8-azabicyclo[3.2.1]oct-2-ene;
(±)-3-[1-(2-Bromophenyl)]-8-methyl-8-azabicyclo[3.2.1]oct-2-ene;
(±)-3-[1-(2-Chlorophenyl)]-8-methyl-8-azabicyclo[3.2.1]oct-2-ene;
(±)-3-[2-(3,4-Dibromothienyl)]-8-methyl-8-azabicyclo[3.2.1]oct-2-ene;
(±)-3-[2-(3,4-Dichlorothienyl)]-8-methyl-8-azabicyclo[3.2.1]oct-2-ene;
(±)-3-[4-(5-Bromothiazolyl)]-8-methyl-8-azabicyclo[3.2.1]oct-2-ene;
(±)-3-[4-(5-Chlorothiazolyl)]-8-methyl-8-azabicyclo[3.2.1]oct-2-ene;
(±)-3-[4-(5-Iodothiazolyl)]-8-methyl-8-azabicyclo[3.2.1]oct-2-ene;
(±)-3-[5-(4-Bromo-1-methyl-imidazolyl)]-8-methyl-8-azabicyclo[3.2.1]oct-2-ene;
(±)-3-[5-(4-Chloro-1-methyl-imidazolyl)]-8-methyl-8-azabicyclo[3.2.1]oct-2-ene;
(±)-3-[5-(4-Iodo-1-methyl-imidzolyl)]-8-methyl-8-azabicyclo[3.2.1]oct-2-ene
(±)-3-[5-(4-Bromo-1-methyl-1,2,3-triazolyl)]-8-methyl-8-azabicyclo[3.2.1]oct-2-ene;
(±)-3-[5-(4-Chloro-1-methyl-1,2,3-triazolyl)]-8-methyl-8-azabicyclo[3.2.1]oct-2-ene;
(±)-3-[5-(4-Iodo-1-methyl-1,2,3-triazolyl)]-8-methyl-8-azabicyclo[3.2.1]oct-2-ene;
(±)-3-[2-(3-Bromo-1-methyl-pyrrolyl)]-8-methyl-8-azabicyclo[3.2.1]oct-2-ene;
(±)-3-[2-(3-Chloro-1-methyl-pyrrolyl)]-8-methyl-8-azabicyclo[3.2.1]oct-2-ene;
(±)-3-[2-(3-Iodo-1-methyl-pyrrolyl)]-8-methyl-8-azabicyclo[3.2.1]oct-2-ene;
(±)-3-[2-(3-Bromoselenophenyl)]-8-methyl-8-azabicyclo[3.2.1]oct-2-ene;
(±)-3-[2-(3-Chloroselenophenyl)]-8-methyl-8-azabicyclo[3.2.1]oct-2-ene;
(±)-3-[2-(3-Iodoselenophenyl)]-8-methyl-8-azabicyclo[3.2.1]oct-2-ene;
(±)-3-[3-(4-Bromo-1-2-5-thiadiazolyl)]-8-methyl-8-azabicyclo[3.2.1]oct-2-ene;
(±)-3-[3-(4-Chloro-1-2-5-thiadiazolyl)]-8-methyl-8-azabicyclo[3.2.1]oct-2-ene;
(±)-3-[3-(4-Iodo-1-2-5-thiadiazolyl)]-8-methyl-8-azabicyclo[3.2.1]oct-2-ene;
(±)-3-[5-(4-Bromo-isoxazolyl)]-8-methyl-8-azabicyclo[3.2.1]oct-2-ene;
(±)-3-[5-(4-Chloro-isoxazolyl)]-8-methyl-8-azabicyclo[3.2.1]oct-2-ene;
(±)-3-[5-(4-Iodo-isoxazolyl)]-8-methyl-8-azabicyclo[3.2.1]oct-2-ene;
(±)-3-[5-(4-Bromo-oxazolyl)]-8-methyl-8-azabicyclo[3.2.1]oct-2-ene;
(±)-3-[5-(4-Chloro-oxazolyl)]-8-methyl-8-azabicyclo[3.2.1]oct-2-ene;
(±)-3-[5-(4-Iodo-oxazolyl)]-8-methyl-8-azabicyclo[3.2.1]oct-2-ene;
(±)-3-[5-(4-Bromo-1-methylpyrazolyl)]-8-methyl-8-azabicyclo[3.2.1]oct-2-ene;
(±)-3-[5-(4-Chloro-1-methylpyrazolyl)]-8-methyl-8-azabicyclo[3.2.1]oct-2-ene;
(±)-3-[5-(4-Iodo-1-methyl pyrazolyl)]-8-methyl-8-azabicyclo[3.2.1]oct-2-ene;
(±)-3-[5-(4-Bromo-isothiazolyl)]-8-methyl-8-azabicyclo[3.2.1]oct-2-ene;
(±)-3-[5-(4-Chloro-isothiazolyl)]-8-methyl-8-azabicyclo[3.2.1]oct-2-ene;
(±)-3-[5-(4-Iodo-isothiazolyl)]-8-methyl-8-azabicyclo[3.2.1]oct-2-ene;
(±)-3-[5-(4-Bromo-furazanyl)]-8-methyl-8-azabicyclo[3.2.1]oct-2-ene;

(±)-3-[5-(4-Chloro-furazanyl)]-8-methyl-8-azabicyclo[3.2.1]oct-2-ene;
(±)-3-[5-(4-Iodo-furazanyl)]-8-methyl-8-azabicyclo[3.2.1]oct-2-ene;
(±)-3-[3-(2-Bromo-pyridyl)]-8-methyl-8-azabicyclo[3.2.1]oct-2-ene;
(±)-3-[3-(2-Chloro-pyridyl)]-8-methyl-8-azabicyclo[3.2.1]oct-2-ene;
(±)-3-[3-(4-Bromo-pyridyl)]-8-methyl-8-azabicyclo[3.2.1]oct-2-ene;
(±)-3-[3-(4-Chloro-pyridyl)]-8-methyl-8-azabicyclo[3.2.1]oct-2-ene;
(±)-3-[4-(3-Bromo-pyridazyl)]-8-methyl-8-azabicyclo[3.2.1]oct-2-ene;
(±)-3-[4-(3-Chloro-pyridazyl)]-8-methyl-8-azabicyclo[3.2.1]oct-2-ene;
(±)-3-[4-(3,6-Dibromo-pyridazyl)]-8-methyl-8-azabicyclo[3.2.1]oct-2-ene;
(±)-3-[4-(3,6-Dichloro-pyridazyl)]-8-methyl-8-azabicyclo[3.2.1]oct-2-ene;
(±)-3-[4-(5-Bromo-pyrimidyl)]-8-methyl-8-azabicyclo[3.2.1]oct-2-ene;
(±)-3-[4-(5-Chloro-pyrimidyl)]-8-methyl-8-azabicyclo[3.2.1]oct-2-ene;
(±)-3-[3-(2,6-dichloropyrazinyl)]-8-methyl-8-azabicyclo[3.2.1]oct-2-ene; and
(±)-3-[3-(2-Chloro-pyrazinyl)]-8-methyl-8-azabicyclo[3.2.1]oct-2-ene.

Intermediate Preparations

2-Bromo-6-methoxynaphthalene:

Sodium hydride (60%, 4.5 g, 112 mmol) was added in small portions to a mixture of 6-bromo-2-naphthol (25.0 g, 112 mmol), iodomethane (11.8 g, 168 mmol) and dimethylsulfoxide (150 ml). The mixture was stirred at room temperature overnight. Sodium hydroxide (200 ml, 1 M) was added, and the mixture was filtered. Yield 25.1 g, 95%. Mp 76–82° C.

2-Bromo-6-methoxymethoxynaphthalene:

Sodium hydride (60%, 4.5 g, 112 mmol) was added in small portions to a mixture of 6-bromo-2-naphthol (25.0 g, 112 mmol), bromomethylmethylether (21.0 g, 168 mmol) and dimethylformamide (150 ml). The mixture was stirred at room temperature for 1 h. Sodium hydroxide (200 ml, 1 M) was added and the mixture was extracted with diethyl ether. The product was purified chromatographically, using dichloromethane as solvent. Yield 15.7 g, 52%. Mp 46.8–49.2° C.

2-Bromo-6-methoxyethoxynaphthol:

Sodium hydride (60%, 5.3 g, 134 mmol) was added in small portions to a mixture of 6-bromo-2-naphthol (25.0 g, 112 mmol), 2-bromoethylmethylether (17.1 g, 123 mmol) and dimethylformamide (150 ml). The mixture was stirred at room temperature for 5 h. Aqueous sodium hydroxide (200 ml, 1 M) was added, and the mixture was allowed to stir overnight. The crystals were filtered. Yield 28.2 g, 89%. Mp 54–55° C.

Example 2

Biological Activity

The affinity of compounds of the invention for nicotinic ACh receptors have been investigated in three test for in vitro inhibition of $^3$H-epibatidin binding, $^3$H-α-bungarotoxin binding and $^3$H-cytisine binding as described below.

In Vitro Inhibition of $^3$H-Cytisine Binding

The predominant subtype with high affinity for nicotine is comprised of $\alpha_4$ and $\beta_2$ subunits. nAChRs of the latter type can selectively be labelled by the nicotinic ACh modulator $^3$H-cytisine.

Tissue Preparation: Preparations are performed at 0–4° C. Cerebral corticies from male Wistar rats (150–250 g) are homogenised for 20 sec in 15 ml Tris, HCl (50 mM, pH 7.4) containing 120 mM NaCl, 5 mM KCl, 1 mM MgCl$_2$ and 2.5 mM CaCl$_2$ using an Ultra-Turrax homogeniser. The homogenate is centrifuged at 27,000×g for 10 min. The supernatant is discarded and the pellet is resuspended in fresh buffer and centrifuged a second time. The final pellet is resuspended in fresh buffer (35 ml per g of original tissue) and used for binding assays.

Assay: Aliquots of 500 μl homogenate are added to 25 μl of test solution and 25 μl of $^3$H-cytisine (1 nM, final concentration), mixed and incubated for 90 min at 2° C. Non-specific binding is determined using (−)-nicotine (100 μM, final concentration). After incubation the samples are added 5 ml of ice-cold buffer and poured directly onto Whatman GF/C glass fibre filters under suction and immediately washed with 2×5 ml ice-cold buffer. The amount of radioactivity on the filters is determined by conventional liquid scintillation counting. Specific binding is total binding minus non-specific binding.

In Vitro Inhibition of $^3$H-α-Bungarotoxin Binding Rat Brain

α-Bungarotoxin is a peptide isolated from the venom of the Elapidae snake Bungarus multicinctus (Mebs et al., Biochem. Biophys. Res. Commun., 44(3), 711 (1971)) and has high affinity for neuronal and neuromuscular nicotinic receptors, where it acts as a potent antagonist. $^3$H-α-Bungarotoxin binds to a single site in rat brain with an unique distribution pattern in rat brain (Clarke et al., J. Neurosci. 5, 1307–1315 (1985)).

$^3$H-α-Bungarotoxin labels nAChR formed by the $\alpha_7$ subunit isoform found in brain and the $\alpha_1$ isoform in the neuromuscular junction (Changeaux, Fidia Res. Found. Neurosci. Found. Lect. 4, 21–168 (1990). Functionally, the $\alpha_7$ homo-oligomer expressed in oocytes has a calcium permeability greater than neuromuscular receptors and, in some instances greater than NMDA channels (Seguela et al., J. Neurosci. 13, 596–604 (1993).

Tissue preparation: Preparations are performed at 0–4° C. Cerebral corticies from male Wistar rats (150–250 g) are homogenised for 10 sec in 15 ml 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is centrifuged at 27,000×g for 10 min. The supernatant is discarded and the pellet is washed twice by centrifugation at 27,000×g for 10 min in 20 ml fresh buffer, and the final pellet is resuspended in fresh buffer containing 0.01% BSA (35 ml per g of original tissue) and used for binding assays.

Assay: Aliquots of 500 μl homogenate are added to 25 μl of test solution and 25 μl of $^3$H-α-bungarotoxin (2 nM, final concentration), mixed and incubated for 2 h at 37° C. Non-specific binding is determined using (−)-nicotine (1 mM, final concentration). After incubation the samples are added 5 ml of ice-cold Hepes buffer containing 0.05% PEI and poured directly onto Whatman GF/C glass fibre filters (presoaked in 0.1% PEI for at least 6 h) under suction and immediately washed with 2×5 ml ice-cold buffer. The amount of radioactivity on the filters is determined by conventional liquid scintillation counting. Specific binding is total binding minus non-specific binding.

In Vitro Inhibition of ³H-Epibatidin Binding

Epibatidin is an alkaloid that was first isolated from the skin of the Ecuadoran frog *Epipedobates tricolor* and was found to have very high affinity for neuronal nicotinic receptors, where it acts as a potent agonist. ³H-epibatidin binds to two sites in rat brain, both of which have pharmacological profiles consistent with neuronal nicotinic receptors and a similar brain regional distribution (Hougling et al., Mol. Pharmacol. 48, 280–287 (1995)).

The high affinity binding site for ³H-epibatidin is most certainly binding to the $\alpha_4\beta_2$ subtype of nicotinic receptors. The identity of the low affinity site is still unknown; does it represent a second nicotinic receptor or a second site in the same receptor. The inability of α-bungarotoxin to compete for ³H-epibatidin binding sites indicates that neither site measured represents the nicotinic receptor composed of α7 subunits.

Tissue preparation: Preparations are performed at 0–4° C. The forebrain (÷cerebellum) from a male Wistar rat (150–250 g) is homogenised for 10–20 sec in 20 ml Tris, HCl (50 mM, pH 7.4) using an Ultra-Turrax homogeniser. The tissue suspension is centrifuged at 27,000×g for 10 min. The supernatant is discarded and the pellet is washed three times by centrifugation at 27,000×g for 10 min in 20 ml fresh buffer, and the final pellet is resuspended in fresh buffer (400 ml per g of original tissue) and used for binding assays.

Assay: Aliquots of 2.0 ml homogenate are added to 0.100 ml of test solution and 0.100 ml of ³H-epibatidin (0.3 nM, final concentration), mixed and incubated for 60 min at room temperature. Non-specific binding is determined using (−)-nicotine (30 μM, final concentration). After incubation the samples are poured directly onto Whatman GF/C glass fibre filters (presoaked in 0.1% PEI for at least 20 min) under suction and immediately washed with 2×5 ml ice-cold buffer. The amount of radioactivity on the filters is determined by conventional liquid scintillation counting. Specific binding is total binding minus non-specific binding.

Results are given as $IC_{50}$ values; the concentration (μM) that inhibit binding of the radioactive ligand by 50%.

What is claimed is:

1. A chemical compound having the formula

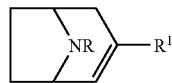

(I)

in labelled or unlabelled form, or any of its enantiomers or any mixture thereof, or a pharmaceutically acceptable salt thereof;

R represents hydrogen, alkyl, alkenyl, alkynyl, cycloalkyl, cycloalkylalkyl, a mono- or polycyclic aryl group, or aralkyl; and R¹ represents a bi-cyclic heterocyclic group selected from the group consisting of 5- or 6-benzimidazolyl, 5- or 6-benzofuranyl, 5- or 6-benzothiazolyl, 5- or 6-benzothienyl, 5- or 6-Benzotriazolyl, 6- or 7-cinnolinyl, 5- or 6-indazolyl, 5- or 6-indolizinyl, 5- or 6-indolyl, 5- or 6- isoindolyl, 6- or 7-isoquinolinyl, 6-phthalazinyl, 6- or 7-quinolinyl, 6- or 7-quinolizinyl, and 6- or 7-quinoxalinyl; which heterocyclic groups may be substituted one or more times with substituents selected from the group consisting halogen, amino, hydroxy, alkoxy, alkoxy-alkyl, alkoxy-alkoxy, sulfanyl, alkylsulfanyl, alkylsulfanyl-alkoxy, alkoxy-alkylsulfanyl, and alkylsulfanyl-alkylsulfanyl.

2. The chemical compound of claim 1, wherein R¹ represents a bi-cyclic heterocyclic group selected from the group consisting of 5- or 6-benzimidazolyl, 5- or 6-benzofuranyl, 5- or 6-benzothiazolyl, 5- or 6-benzothienyl, 5- or 6-Benzotriazolyl, 6- or 7-cinnolinyl, 5- or 6-indazolyl, 5- or 6-indolizinyl, 5- or 6-indolyl, 5- or 6-isoindolyl, 6- or 7-isoquinolinyl, 6-phthalazinyl, 6- or 7-quinolinyl, 6- or 7-quinolizinyl, and 6- or 7-quinoxalinyl; which heterocyclic groups may be substituted one or more times with substituents selected from the group consisting of halogen, amino, hydroxy, alkoxy, alkoxy-alkyl, alkoxy-alkoxy, sulfanyl, alkylsulfanyl, alkylsulfanyl-alkoxy, alkoxy-alkylsulfanyl, and alkylsulfanyl-alkylsulfanyl.

3. A compound selected from the group consisting of:
(±)-3-[6-Isoquinolinyl]-8-methyl-8-azabicyclo[3.2.1]oct-2-ene;
(±)-3-[6-Quinolinyl]-8-methyl-8-azabicyclo[3.2.1]oct-2-ene;
(±)-3-[7-Isoquinolinyl]-8-methyl-8-azabicyclo[3.2.1]oct-2-ene;
(±)-3-[7-Quinolinyl]-8-methyl-8-azabicyclo[3.2.1]oct-2-ene;
(±)-3-[1-H-5-Benzimidazolyl]-8-methyl-8-azabicyclo[3.2.1]oct-2-ene;
(±)-3-[1-H-6-Benzimidazolyl]-8-methyl-8-azabicyclo[3.2.1]oct-2-ene;
(±)-3-[1-H-5-Benzotriazolyl]-8-methyl-8-azabicyclo[3.2.1]oct-2-ene;
(±)-3-[1-H-6-Benzotriazolyl]-8-methyl-8-azabicyclo[3.2.1]oct-2-ene;
(±)-3-[2-Amino-1-H-5-benzimidazolyl]-8-methyl-8-azabicyclo[3.2.1]oct-2-ene;
(±)-3-[2-Amino-1-H-6-benzimidazolyl]-8-methyl-8-azabicyclo[3.2.1]oct-2-ene;
(±)-3-[6-phthalazinyl]-8-methyl-8-azabicyclo[3.2.1]oct-2-ene;
(±)-3-[5-Benzofuranyl]-8-methyl-8-azabicyclo[3.2.1]oct-2-ene;
(±)-3-[6-Benzofuranyl]-8-methyl-8-azabicyclo[3.2.1]oct-2-ene;
(±)-3-[5-Benzothienyl]-8-methyl-8-azabicyclo[3.2.1]oct-2-ene;
(±)-3-[6-Benzothienyl]-8-methyl-8-azabicyclo[3.2.1]oct-2-ene;
(±)-3-[5-Benzothiazolyl]-8-methyl-8-azabicyclo[3.2.1]oct-2-ene;
(±)-3-[6-Benzothiazolyl]-8-methyl-8-azabicyclo[3.2.1]oct-2-ene;
(±)-3-[1-Methyl-5-indolyl]-8-methyl-8-azabicyclo[3.2.1]oct-2-ene;
(±)-3-[1-Methyl-6-indolyl]-8-methyl-8-azabicyclo[3.2.1]oct-2-ene;
(±)-3-[5-Indolizinyl]-8-methyl-8-azabicyclo[3.2.1]oct-2-ene;
(±)-3-[6-Indolizinyl]-8-methyl-8-azabicyclo[3.2.1]oct-2-ene;
(±)-3-[2-Methyl-5-isoindolyl]-8-methyl-8-azabicyclo[3.2.1]oct-2-ene;
(±)-3-[2-Methyl-6-isoindolyl]-8-methyl-8-azabicyclo[3.2.1]oct-2-ene;
(±)-3-[1-Methyl-5-indazolyl]-8-methyl-8-azabicyclo[3.2.1]oct-2-ene;
(±)-3-[1-Methyl-6-indazolyl]-8-methyl-8-azabicyclo[3.2.1]oct-2-ene;

(±)-3-[6-Quinolizinyl]-8-methyl-8-azabicyclo[3.2.1]oct-2-ene;
(±)-3-[7-Quinolizinyl]-8-methyl-8-azabicyclo[3.2.1]oct-2-ene;
(±)-3-[6-Cinnolinyl]-8-methyl-8-azabicyclo[3.2.1]oct-2-ene;
(±)-3-[7-Cinnolinyl]-8-methyl-8-azabicyclo[3.2.1]oct-2-ene;

(±)-3-[6-Quinoxalinyl]-8-methyl-8-azabicyclo[3.2.1]oct-2-ene; or
(±)-3-[7-Quinoxalinyl]-8-methyl-8-azabicyclo[3.2.1]oct-2-ene;

or a pharmaceutically acceptable addition salt thereof.

* * * * *